US008481789B2

(12) United States Patent
Mane et al.

(10) Patent No.: US 8,481,789 B2
(45) Date of Patent: Jul. 9, 2013

(54) METHOD FOR PRODUCING NATURAL 9-DECEN-2-ONE BY BIOCONVERTING UNDECYLENIC ACID USING A MOLD, AND USE IN THE PERFUME AND FOOD FLAVORING FIELDS

(75) Inventors: Jean Mane, Grasse (FR); Joseph Zucca, Grasse, (FR)

(73) Assignee: V. Mane Fils, Bar sur Loup (FR)

( * ) Notice: Subject to any disclaimer, the term of this patent is extended or adjusted under 35 U.S.C. 154(b) by 97 days.

(21) Appl. No.: 12/995,289

(22) PCT Filed: Jun. 3, 2009

(86) PCT No.: PCT/FR2009/000646
§ 371 (c)(1),
(2), (4) Date: Nov. 30, 2010

(87) PCT Pub. No.: WO2009/147319
PCT Pub. Date: Dec. 10, 2009

(65) Prior Publication Data
US 2011/0077431 A1    Mar. 31, 2011

(30) Foreign Application Priority Data

Jun. 3, 2008  (FR) ...................................... 08 53672

(51) Int. Cl.
*C07C 49/203* (2006.01)
*A23L 1/23* (2006.01)
(52) U.S. Cl.
USPC .......................................... 568/417; 435/148

(58) Field of Classification Search
USPC .......................................... 568/417; 435/148
See application file for complete search history.

(56) References Cited

U.S. PATENT DOCUMENTS

| 4,832,964 A | 5/1989 | Pratt |
| 4,957,862 A | 9/1990 | Creuly et al. |
| 2008/0125345 A1 | 5/2008 | Zucca et al. |

FOREIGN PATENT DOCUMENTS

| JP | 59039822 | 3/1984 |
| JP | 2265495 | 10/1990 |
| JP | 4148688 | 5/1992 |

OTHER PUBLICATIONS

Database WPI Week 198415 Thomson Scientific, London, GB; AN 1984-092349 XP002524503.
Database WPI Week 199227 Thomson Scientific, London, GB; AN 1992-223243 XP002524501.
Database CA [Online] Chemical Abstracts Service, Columbus, Ohio, US; Nov. 1, 1992 XP002524499, Database accession No. 117:169602.
Database WPI Week 199049 Thomson Scientific, London, GB; AN 1990-366323 XP002524502.
Database CA [Online] Chemical Abstracts Service, Columbus, Ohio, US; May 31, 1991 XP002524500 Database accession No. 114:205568.
Forney F.W. et al, "The biology of methyl ketones.", Jul. 1971, pp. 383-395, vol. 12, No. 4, Journal of Lipid Research.

*Primary Examiner* — Sikarl Witherspoon
(74) *Attorney, Agent, or Firm* — B. Aaron Schulman, Esq.; Stites & Harbison, PLLC

(57) ABSTRACT

The present invention relates to a process for producing 9-decen-2-one, characterized by the bioconversion of undecylenic acid using a mold, and to its use in perfumery, cosmetics and food flavoring.

22 Claims, 1 Drawing Sheet

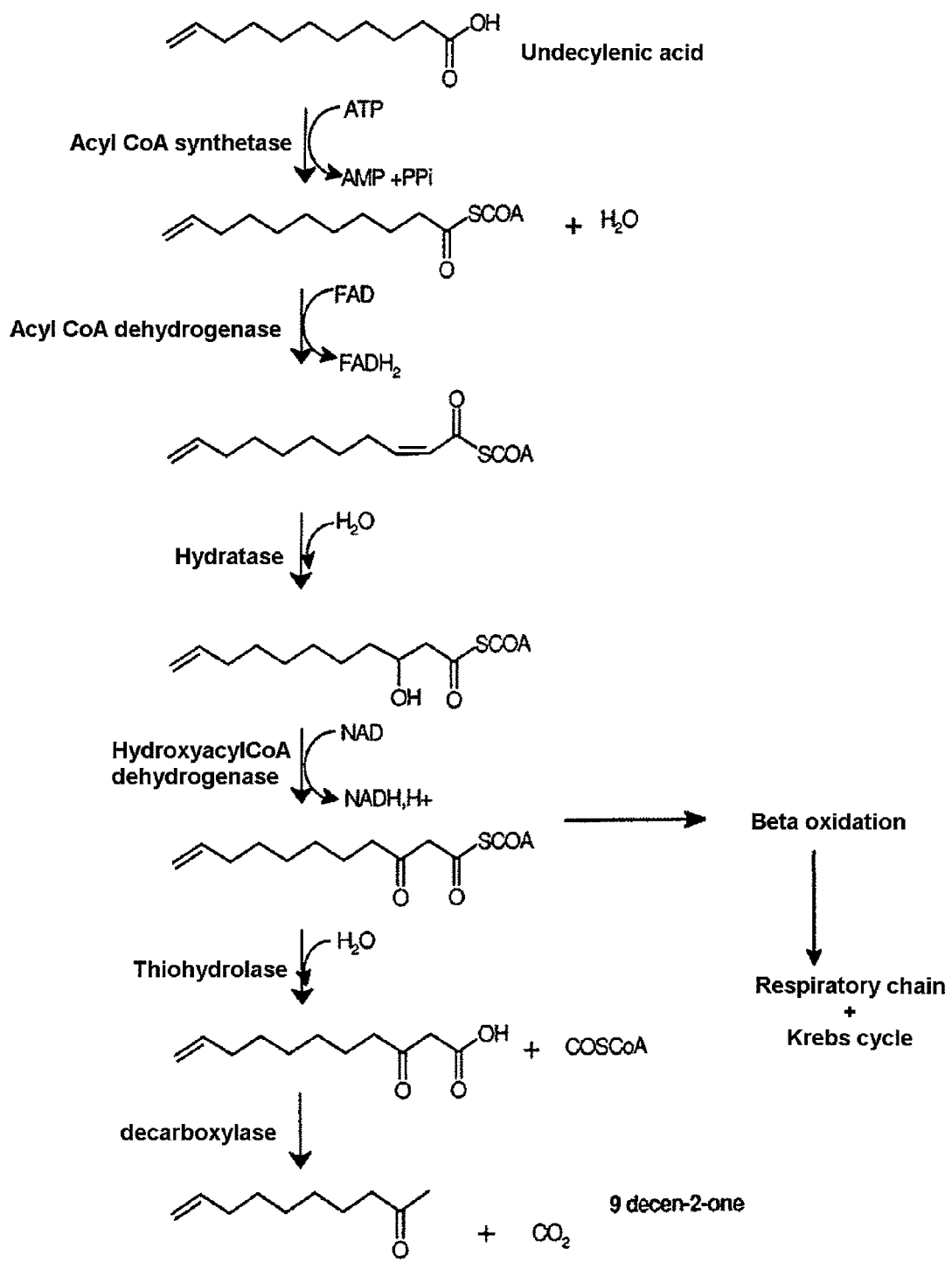

METHOD FOR PRODUCING NATURAL 9-DECEN-2-ONE BY BIOCONVERTING UNDECYLENIC ACID USING A MOLD, AND USE IN THE PERFUME AND FOOD FLAVORING FIELDS

The present invention relates to the bioconversion, using a mold, of undecylenic acid into 9-decen-2-one, this product being able to be used in fragrancing and food flavoring applications.

The Applicant Company has demonstrated that 9-decen-2-one (or 2-decenone or methyl octenyl ketone, RN CAS 35194-30-0) is a methyl ketone with olfactory and taste properties such that it may be used in all applications of the aromatics industry (flavorings and fragrances). Specifically, it has a green and fatty note and also fruity notes, especially of pear, apple, pineapple, passion fruit and exotic fruit in general.

This ketone, just like other methyl ketones, is formed via a metabolic pathway that involves the first steps of β-oxidation after fatty acid oxidation. This metabolic pathway for the formation of methyl ketones is used by mycetes during the detoxification of fatty acids.

As may be observed by the representation of the metabolic pathway (FIG. 1), the substrate used in the bioconversion is undecylenic acid, which is obtained by cracking (physical operation that transforms the crude product into finer compounds) of ricinoleic acid obtained from castor oil and then purified by a dry distillation. Finally, after a decarboxylation step, the methyl ketone obtained at the end of the pathway contains one carbon less than the original fatty acid.

To the Applicant Company's knowledge, there is at the present time no biotechnological process that describes and/or allows the synthesis of 9-decen-2-one. Specifically, this molecule can only be obtained at the present time via chemical synthesis, and in mediocre yields. Moreover, synthetic flavorings have the drawback of being less appreciated by consumers than natural flavorings. Consequently, the aim of the present invention is to provide an alternative process for obtaining natural aromatic molecules, in particular those obtained via 9-decen-2-one, by means of biological processes, especially bioconversion, using microorganisms such as molds.

For the purposes of the present invention, the term "bioconversion" means the biological transformation of a substrate, preferably derived from a natural source, to obtain natural flavoring substances that may be formulated in flavorings or fragrances termed as being natural.

The Applicant Company has found, surprisingly and unexpectedly, that it is possible to satisfy this objective by means of a process for producing 9-decen-2-one, characterized by the bioconversion of undecylenic acid using a mold, said process comprising the following steps:
  a) culturing said mold;
  b) adding undecylenic acid as bioconversion substrate, in the present of oil;
  c) bioconverting the substrate into 9-decen-2-one;
  d) extracting and purifying the 9-decen-2-one.

For the purposes of the present invention, the term "mold" corresponds to unicellular or multicellular filamentous microscopic fungi. Among molds, Phycomycetes and Septomycetes are distinguished. Among the Phycomycetes are the phylum of Oomycotineae and the phylum of Zygomycotineae. Within the Septomycetes are the phylum of Ascomycotineae, the phylum of Basidiomycotineae and the phylum of Deuteromycotineae.

In one embodiment of the invention, the mold according to the invention belongs to the phylum of Deuteromycotineae, class of Hyphomycetes, order of Tuberculariales, family of Aspergillaceae. More preferably, said mold belongs to the genus *Aspergillus* or *Penicillium*. In a first preferred embodiment, said mold belongs to the species *Aspergillus oryzae* or to the species *Aspergillus niger*. In a second preferred embodiment, said mold belongs to the species *Penicillium roquefortii* or to the species *Penicillium camembertii*.

Among the *Aspergillus oryzae* molds, mention may be made of the following collection strains: *Aspergillus oryzae* DSMZ 1861, *Aspergillus oryzae* DSMZ 1864, *Aspergillus oryzae* DSMZ 1147, *Aspergillus oryzae* DSMZ 63303, *Aspergillus oryzae* CBS 570.65, *Aspergillus oryzae* CBS 819.72, *Aspergillus oryzae* CBS 110.27.

Among the *Aspergillus niger* molds, mention may be made of the following collection strains: *Aspergillus niger* DSMZ 823, *Aspergillus niger* DSMZ 2466.

Among the *Penicillium roquefortii* molds, mention may be made of the following collection strains: *Penicillium roquefortii* CBS 221-30, *Penicillium roquefortii* PRB 18, *Penicillium roquefortii* DSMZ 1079, *Penicillium roquefortii* DSMZ 1080.

Among the *Penicillium camembertii* molds, mention may be made of the strain *Penicillium camembertii* DSMZ 1233.

According to another preferred embodiment, the mold according to the invention belongs to the phylum of Zygomycotineae, class of Zygomycetes, order of Mucorales, family of Mortierellaceae or family of Mucoraceae.

More preferably, said mold belongs to the genus *Mortierella* or to the genus *Mucor* or to the genus *Rhizopus*, and even more preferably said mold belongs to the species *Mortierella isabellina* or *Mortierella ramanniana* or to the species *Mucor racemosus* or *Mucor miehei* or to the species *Rhizopus arrhizus* or *Rhizopus oryzae*.

Among the molds belonging to the genus *Mortierella*, mention may be made of the following collection strains: *Mortierella isabellina* DSMZ 1414, *Mortierella isabellina* CBS 100559, *Mortierella isabellina* CBS 221.29, *Mortierella isabellina* CBS 194.28, *Mortierella isabellina* CBS 208.32, *Mortierella isabellina* CBS 224.35, *Mortierella isabellina* CBS 560.63, *Mortierella isabellina* CBS 167.80, *Mortierella isabellina* CBS 493.83, *Mortierella isabellina* CBS 309.93, *Mortierella isabellina* CBS 250.95, *Mortierella isabellina* CBS 109075, *Mortierella ramanniana* CBS 112.08, *Mortierella ramanniana* CBS 219.47, *Mortierella ramanniana* CBS 243.58, *Mortierella ramanniana* CBS 478.63, *Mortierella* ramanniana CBS 852.72, *Mortierella ramanniana* CBS 366.95, *Mortierella ramanniana* CBS 101226.

Among the molds belonging to the genus *Mucor*, mention may be made of the following collection strains: *Mucor javanicus* DSMZ 1222, *Mucor racemosus* DSMZ 62760, *Mucor rouxii* DSMZ 1191.

Among the molds belonging to the genus *Rhizopus*, mention may be made of the following collection strains: *Rhizopus arrhizus* oryzae DSMZ 905, *Rhizopus* oryzae DSMZ 2199, *Rhizopus delemar* DSMZ 853, *Rhizopus niveus* DSMZ 2194, *Rhizomucor miehei* DSMZ 1330.

The culturing targeted in step a) of the process according to the invention involves the preparation of a culture, preferably semi-concentrated, for example by cell amplification, in a suitable culture medium. This culturing is preceded by pre-culturing of the strain in a first culture medium that is more suited to the first multiplication steps.

In one preferred embodiment of the invention, the time for culturing said mold ranges between 20 and 30 hours and in fact depends on the state of growth of the mycelium, the latter possibly being observed by microscope. It is in point of fact preferred for the minimum biomass of the mold to be between 7 and 15 g/l and more preferably between 9 and 12 g/l, before performing the bioconversion according to the invention.

Step b) of the process consists in adding the substrate to the cell culture. According to the invention, the biological synthesis of 9-decen-2-one involves the most suitable substrate, which is undecylenic acid or an ester thereof, the methyl ester or the ethyl ester of undecylenic acid. It goes without saying that the substrate may be a mixture of different suitable substrates, in particular a mixture of undecylenic acid and of one or more of its esters.

According to one advantageous embodiment of the invention, the substrate is added to the mycelium in a batch or fed-batch process.

In one preferred embodiment of the invention, said undecylenic acid is added to the fermentation medium at a feed rate of from 0.1 to 0.9 g/l/h, preferably from 0.2 to 0.7 g/l/h and most preferentially from 0.3 to 0.55 g/l/h.

Step c) of the process consists of the bioconversion of undecylenic acid into 9-decen-2-one.

The duration of this bioconversion phase is generally from 36 to 96 hours.

On account of the high toxicity of undecylenic acid toward mycetes, an adaptation period may prove to be necessary in order to prepare the mold for converting the substrate. Thus, according to one preferred embodiment, the bioconversion step of the process according to the invention comprises a first phase of adaptation of the mold in which said undecylenic acid is added at a feed rate of 0.1 to 0.5 g/l/h, followed by a second phase in which the undecylenic acid is added at a feed rate of 0.25 to 0.9 g/l/h. Advantageously, the duration of said adaptation phase is less than 20 hours, preferably less than 12 hours and more preferentially less than 6 hours.

According to one preferred embodiment, the undecylenic acid is added in the presence of oil. Said oil may be chosen from the group comprising standard food-grade oils such as soybean oil, corn oil, sunflower oil or the like, or triglycerides containing short-chain fatty acids such as Miglyol, or alternatively white oils such as liquid paraffin or mineral oils composed of long-chain hydrocarbons. Preferably, said oil is sunflower oil that is partially hydrogenated or rich in oleic acid.

Preferably, said oil is added in the following proportions relative to the substrate: undecylenic acid/oil=¼ undecylenic acid—¾ oil or ⅓ undecylenic acid—⅔ oil or ½ undecylenic acid—½ oil.

Advantageously, said oil is added to the fermentation medium at a feed rate of 0.4 to 4.0 g/l/h, preferably from 0.5 to 3 g/l/h and most preferentially from 0.75 to 2.5 g/l/h.

Like all types of microorganisms in a situation of forced bioconversion, mycetes need a carbon source to cover their energy needs, for instance a source of carbohydrate, preferably glucose or maltose. The provision of glucose during the bioconversion is preferred. Consequently, according to another preferred embodiment of the invention, glucose or maltose is added simultaneously with the undecylenic acid and the oil. Advantageously, said glucose or said maltose is added to the fermentation medium at a feed rate of less than 1 g/l/h, preferably less than 0.75 g/l/h and most preferentially less than 0.5 g/l/h.

According to another preferred embodiment of the invention, the addition of said undecylenic acid, of said oil and optionally of said glucose or maltose to the fermentation medium is formed continuously for 5 to 96 hours, preferably for 24 to 72 hours and more preferably for 24 to 48 hours.

According to another preferred embodiment, the bioconversion according to the invention is performed at a temperature of between 25° C. and 35° C. and preferably between 27 and 30° C.

According to another preferred embodiment, the pH of the fermentation medium according to the invention is from 5 to 8, preferably from 5.5 to 7.5 and more preferentially from 6 to 7. In the context of the invention, regulation of the pH is performed using sodium hydroxide (for example sterile 5N NaOH or another standard fermentation base ($NH_4OH$, KOH, etc.)).

During the bioconversion, it is important to have good stirring and also good aeration of the fermentation medium. In the fermenter, stirring may be achieved by means of several stirring paddles. Advantageously and according to the size of the fermenter, for example for a 6 liter fermenter, the adequate stirring necessary according to the invention is from 200 to 1200 rpm and preferably from 300 to 900 rpm. The aeration, for its part, may be achieved by injecting air into the stirring paddles. Advantageously, the adequate aeration of the fermentation medium according to the invention is less than or equal to 1 vvm, preferably between 0.2 and 0.8 vvm and more preferentially between 0.3 and 0.7 vvm.

In another preferred embodiment, the bioconversion according to the invention is stopped by adding an acid to the culture medium. Said acid may be chosen from the group comprising phosphoric acid, sulfuric acid, hydrochloric acid and citric acid. Preferably, said acid is phosphoric acid or citric acid.

In step d), the extraction of the 9-decen-2-one may be performed by hydrodistillation or by extraction using a solvent chosen from the group comprising cyclohexane, methylcyclohexane and ethyl acetate. Preferably, the solvent used is cyclohexane or a cyclohexane/ethyl acetate mixture.

Purification of the 9-decen-2-one may then be performed by deresination followed by fractional distillation.

This extraction/purification process thus makes it possible to obtain a molecule that is more than 98% pure in an extraction yield of about 75% to 85%.

The bioconversion yield into 9-decen-2-one relative to the substrate used, undecylenic acid, is about 25% to 35%.

The invention also relates to the 9-decen-2-one obtained by the process as described above.

A subject of the invention is the use of 9-decen-2-one (CAS 35194-30-0) in all the applications of perfumery and food flavoring, in particular for the manufacture of perfumes, odorous materials, cosmetic or food compositions, or as food additives.

In one preferred embodiment, a subject of the invention is the use of 9-decen-2-one obtained via the process as described above in all the applications of perfumery and food flavoring, in particular for the manufacture of perfumes, odorous materials, cosmetic or food compositions, or as food additives.

For the purposes of the present invention, the term "perfumery" denotes not only perfumery in the usual sense of the term, but also the other fields in which the odor of products is important. This may be, without the following being limiting, perfumery compositions in the usual sense of the term, such as perfuming bases and concentrates, eaux de Cologne, eaux de toilette, perfumes and similar products; topical compositions—in particular cosmetic compositions—such as face and body creams, talcum powders, hair oils, shampoos, hair lotions, ointments, bath salts and oils, shower and bath gels, toiletry soaps, antiperspirants and body deodorants, shaving lotions and creams, soaps, creams, toothpastes, mouthwashes, pomades, and similar products; and household products such as softeners, detergents, laundry products, ambient deodorizers, aerosols and similar products.

The term "odorous" is used to denote a compound that gives off an odor.

The term "food flavoring" means any use of the compounds of the invention for flavoring any human or animal, liquid or solid foodstuff, especially drinks, dairy products, ice creams, sweets, chewing gums, etc., but also for flavoring tobacco.

9-Decen-2-one may thus be used in perfuming compositions or in food flavoring compositions to contribute toward giving exotic, floral or fruity notes, in particular pineapple, pear, passion fruit or exotic fruit. Depending on the application, this molecule 9-decen-2-one will be used in proportions determined by a person skilled in the art.

Preferably, the 9-decen-2-one will be used in amounts of between 0.00025% and 30%, preferably between 0.0025% and 20% and more preferably between 0.025% and 10% by weight relative to the total weight of the composition in which it is present. It may be included in the composition of solids or liquids and especially in the composition of gels, creams, pomades and/or sprays.

9-Decen-2-one may also be used in a composition that is itself odorous, or in a composition in which the odorous agent is used to mask or neutralize certain odors.

Other aspects, subjects, advantages and characteristics of the invention will be presented on reading the non-limiting description that follows and that describes preferred embodiments and of the invention given by means of the following examples.

FIG. 1 describes the bioconversion of undecylenic acid into 9-decen-2-one.

EXAMPLES

Example 1

The strains *Mortierella isabellina* (A), *Aspergillus oryzae* (B) and *Penicillium roquefortii* (C) [origin=tube frozen at −80° C.] are seeded onto malt agar, and incubated at 27° C. (for A) or 30° C. (for B and C) for 72 hours.

The preceding preculture is seeded into 3.5 l of malt medium in a 6 l fermenter:
malt extract: 50 g/l
yeast extract: 7.5 g/l
pH 6.5
*Mortierella isabellina* (A)
Said strain is incubated for 24 hours at 27° C., the stirring is 500 rpm and the aeration is 0.3 vvm.
*Aspergillus oryzae* (B)
Said strain is incubated for 24 hours at 30° C., the stirring is 600 rpm and the aeration is 0.5 vvm.
*Penicillium roquefortii* (C)
Said strain is incubated for 24 hours at 30° C., the stirring is 600 rpm and the aeration is 0.3 vvm.

The dry weight of mycelium at the end of culturing for each strain is about 9 to 11 g/l.

The undecylenic acid is then dispensed at a feed rate of 0.15 g/l/h for 6 hours and then at a feed rate of 0.33 g/l/h for 72 hours: i.e. a total of 25 g/l. This undecylenic acid is dispensed as a mixture with hydrogenated sunflower oil (⅓ acid-⅔ oil); this oil is thus dispensed at feed rates of 0.6 g/l/h and then 1 g/l/h. Glucose is dispensed in parallel continuously at a feed rate of 0.36 g/l/h for 72 hours. The pH is regulated at 6.5 throughout the conversion with 5N NaOH. The speed is increased to 900 rpm and the culture is aerated at a rate of 1 vvm for *Mortierella isabellina* and at 0.3 vvm for *Aspergillus oryzae* or *Penicillium roquefortii*. The conversion is continued for 72 hours.

Under nonoptimized conditions, a production of between 5 and 7 g/l of 9-decen-2-one is obtained.

Example 2

Conversion with *Aspergillus oryzae* (B)

*Aspergillus oryzae* [origin=tube frozen at −80° C.] is seeded onto malt agar, and incubated at 30° C. for 72 hours.

The preceding preculture is seeded into 3.5 l of malt medium (same concentration as in Example 1).

The mixture is incubated at 30° C., 600 rpm, 0.5 vvm of air, free pH, for 24 hours. A dry weight of 11 g/l is obtained.

The undecylenic acid is then dispensed at a feed rate of 0.5 g/l/h for 6 hours and then at a feed rate of 0.9 g/l/h for 48 hours: i.e. a total of 46 g/l. This undecylenic acid is dispensed as a mixture with hydrogenated sunflower oil (¼ acid-¾ oil); this oil is thus dispensed at feed rates of 1.5 g/l/h and then 2.7 g/l/h. Glucose is dispensed in parallel continuously at a feed rate of 0.36 g/l/h for 48 hours. The pH is regulated at 6 throughout the conversion with 5N NaOH. The speed is increased to 900 rpm and the mixture is aerated at a rate of 0.3 vvm. The conversion is continued for 48 hours.

A production of 16.5 g/l of 9-decen-2-one is obtained, i.e. a bioconversion yield of 35%.

Example 3

Conversion with *Mortierella isabellina* (A)

*Mortierella isabellina* [origin=tube frozen at −80° C.] is seeded onto malt agar, and incubated at 27° C. for 72 hours.

The preceding preculture is seeded into 3.5 l of malt medium (same concentration as in Example 1).

The mixture is incubated for 24 hours at 27° C., the stirring is 600 rpm and the aeration is 0.5 vvm. A dry weight of 11.3 g/l is obtained.

The undecylenic acid is then dispensed at a feed rate of 0.27 g/l/h for 6 hours and then at a feed rate of 0.477 g/l/h for 48 hours: i.e. a total of 46 g/l. This undecylenic acid is dispensed as a mixture with hydrogenated sunflower oil (¼ acid-¾ oil); this oil is thus dispensed at feed rates of 0.8 g/l/h and then 1.43 g/l/h. Glucose is dispensed in parallel continuously at a feed rate of 0.32 g/l/h for 48 hours. The pH is regulated to 7.5 throughout the conversion with 5N NaOH. The speed is increased to 900 rpm and the mixture is aerated at a rate of 1 vvm. The conversion is continued for 48 hours.

A production of 8 g/l of 9-decen-2-one is obtained, i.e. a bioconversion yield of 33%.

Example 4

Conversion with *Penicillium roquefortii* (C)

*Penicillium roquefortii* [origin=tube frozen at −80° C.] is seeded onto malt agar, and incubated at 30° C. for 72 hours.

The preceding preculture is seeded into 3.5 l of malt medium (same concentration as in Example 1).

The mixture is incubated for 22 hours at 30° C., the stirring is 600 rpm and the aeration is 0.3 vvm. A dry weight of 10 g/l is obtained.

The undecylenic acid is then redispensed at a feed rate of 0.25 g/l/h for 6 hours and then at a feed rate of 0.45 g/l/h for 48 hours, and then at a feed rate of 0.25 g/l/h for 24 hours: i.e.

a total of about 30 g/l. This undecylenic acid is dispensed as a mixture with hydrogenated sunflower oil (⅓ acid-⅔ oil); this oil is thus dispensed at feed rates of 0.5 g/l/h, then 0.9 g/l/h and then 0.5 g/l/h. Glucose is dispensed in parallel continuously at a feed rate of 0.36 g/l/h for 72 hours. The pH is regulated to 6.5 throughout the conversion with 5N NaOH. The speed is increased to 900 rpm and the mixture is aerated at a rate of 0.6 vvm. The conversion is continued for 48 hours.

A production of 10.5 g/l of 9-decen-2-one is obtained, i.e. a bioconversion yield of 35%.

Example 5

Extraction—Purification

Acidification to pH 1.5 to 2 is performed with 85% phosphoric acid. The extraction solvent cyclohexane is added and stirring is performed for 1 hour at room temperature. The mixture is centrifuged and the organic phase is recovered. The methyl ketone is assayed. The solvent is concentrated and an oily "crude product" is thus obtained. It is distilled under vacuum. The "deresinated" lactone and a depleted oil are obtained. Purification is then performed by fractionating the molecule under vacuum. A product that is more than 99% pure is obtained.

Example 6

Evaluation of the 9-decen-2-one in Perfumery

The 99% pure 9-decen-2-one was tested on smelling paper and in solution (at 5% in ethanol): the head note is powerful, homogeneous, with rose, aldehydic, citronellyl acetate and coriander leaf notes and marine notes. The base has pear notes.

Example 7

Evaluation in Food Flavoring

The 99% pure 9-decen-2-one was tested at 8 ppm in mineral water: it has fruity notes: pear, apple and pineapple, and green and fatty notes.

It was judged to be advantageous for adding sophistication to natural exotic fruit formulations, all the more so since there are not many natural molecules available for achieving this aim. In particular, the "pineapple" tonality of 9-decen-2-one constitutes a very attractive alternative for replacing allyl caproate, which is the molecule that is currently most widely used in formulation for obtaining a tonality of pineapple type.

Example 8

Use in Formulation in Food Flavoring and in Perfumery

In an exotic fruit flavoring, the addition of 9-decen-2-one makes it possible to obtain a typically "pineapple" tonality.

In the following formula, the weight-for-weight replacement of allyl caproate, usually used in formulation, by 9-decen-2-one makes it possible to compensate very advantageously for the "pineapple" tonality afforded by allyl caproate.

| | |
|---|---|
| natural ethyl caproate | 50 g |
| natural maltol | 20 g |
| natural isoamyl acetate | 35 g |
| natural ethyl isovalerate | 37 g |
| natural menthol codex | 8 g |
| natural ethyl methyl-2-butyrate | 75 g |
| natural ethyl acetate | 50 g |
| natural isoamyl butyrate | 12 g |
| natural ethyl butyrate | 35 g |
| refined camphor | 2 g |
| natural 9-decen-2-one | 200 g |
| natural ethyl alcohol | qs. 1000 g |

The use at 50 ppm of this mixture in a still drink with juice gives it very characteristic "pineapple" notes; the same is true when this mixture is used at 200 ppm to give a sorbet "pineapple" character.

Still in natural food flavoring formulation, 9-decen-2 one makes it possible to obtain advantageous "pear" notes, for example in the following formula:

| | |
|---|---|
| natural caproic acid | 1 to 10 g |
| natural isoamyl alcohol | 20 to 60 g |
| natural hexyl alcohol | 10 to 50 g |
| natural ethyl caprate | 20 to 80 g |
| natural ethyl caprylate | 50 to 150 g |
| natural isoamyl acetate | 50 to 150 g |
| natural propyl acetate | 50 to 150 g |
| natural hexyl acetate | 50 to 150 g |
| natural butyl acetate | 50 to 150 g |
| natural ethyl acetate | 50 to 150 g |
| natural 9-decen-2-one | 20 to 50 g |
| propylene glycol | qs. 1000 g |

The use at 100 ppm of this mixture in a drink sparingly sweetened to 5% and slightly acidified (0.1% citric acid) gives it very characteristic "pear" notes, even if the dose of 9-decen-2-one is very low (2 to 5 ppm).

In perfumery formulation, 9-decen-2-one makes it possible to push the "flowery, green, violet" side and the "aldehydic fruity" note of a shampoo, for example in the following formula in which 9-decen-2-one is used at 1%, which makes the perfume note of the shampoo more complex and more round:

| | |
|---|---|
| benzyl acetate | 70 g, |
| phenylethyl alcohol | 100 g, |
| γ-undecalactone | 4 g, |
| cis-isoambrettolide | 10 g, |
| anisaldehyde | 25 g, |
| bacdanol | 80 g, |
| citronellol | 85 g, |
| ethylvanillin | 2 g, |
| geraniol | 40 g, |
| methyl dihydrojasmonate | 120 g, |
| oxacyclohexadecen-2-one | 100 g, |
| heliotropin | 20 g, |
| 2-acetyl-1,2,3,4,5,6,7,8-octa-hydro-2,3,8,8-tetra-methylnaphthalene | 110 g, |
| isoeugenol | 2 g, |
| 4-(1,1-dimethylethyl)-α-methylbenzene-propanal | 110 g, |
| linalool | 60 g, |
| methyl ionone | 30 g, |
| vanillin | 10 g, |
| 2-octynoic acid, methyl ester | 12 g, |
| 9-decen-2-one | 10 g, |
| Total | 1000 g. |

In the case of a different application in perfumery, that of a softener, the presence of 9-decen-2-one dosed at 0.5% gives the power and pushes the "apple" and "pear" fruity side of the softener fragrance, as indicated in the following formula:

| | |
|---|---|
| benzyl acetate | 70 g, |
| phenoxyallyl acetate | 30 g, |
| phenylethyl alcohol | 80 g, |
| hexylcinnamaldehyde | 40 g, |
| C12 aldehyde | 2 g, |
| cis-isoambrettolide | 60 g, |
| anisaldehyde | 30 g, |
| 2-cyclohexylidene-2-phenylacetonitrile | 20 g, |
| bacdanol | 50 g, |
| citronellol | 50 g, |
| coumarin | 80 g, |
| dihydromyrcenol | 100 g, |
| acetic acid, 3a,4,5,6,7,7a-hexahydro-4,7-methano-1H-indenyl ester | 65 g, |
| 2-acetyl-1,2,3,4,5,6,7,8-octahydro-2,3,8,8-tetramethylnaphthalene | 106 g, |
| methylionantheme | 40 g, |
| patchouli essence | 30 g, |
| cyclohexyl salicylate | 100 g, |
| dimethyl 3-cyclohexene-1-carboxaldehyde | 8 g, |
| Ambroxan 5% DPG | 6 g, |
| Galbanum essence 10% DPG | 10 g, |
| indole 10% DPG | 8 g, |
| 9-decen-1-ol 10% DPG | 10 g, |
| 9-decen-2-one | 5 g, |
| Total | 1000 g. |

Finally, in the case of a cream, 9-decen-2-one gives the cream accentuated floral notes, for example in the following application:

| | |
|---|---|
| benzyl acetate | 49 g, |
| cis-3-hexenyl acetate | 2 g, |
| linalyl acetate | 85 g, |
| phenylethyl alcohol | 65 g, |
| γ-undecalactone | 6 g, |
| allyl amyl glycolate | 20 g, |
| methyl anthranilate | 5 g, |
| anisaldehyde | 10 g, |
| methylbenzoate | 8 g, |
| citronellol | 45 g, |
| ethylvanillin | 11 g, |
| geraniol | 35 g, |
| methyl hydrojasmonate | 130 g, |
| heliotropin | 5 g, |
| cis-3-hexenol | 2 g, |
| α-ionone | 23 g, |
| β-ionone | 4 g, |
| 2-acetyl-1,2,3,4,5,6,7,8-octahydro-2,3,8,8-tetramethylnaphthalene | 75 g, |
| 4-(1,1-dimethylethyl)-α-methyl-benzenepropanal | 70 g, |
| linalool | 100 g, |
| patchouli essence | 11 g, |
| γ-nonalactone | 27 g, |
| cis-3-hexenyl salicylate | 35 g, |
| hexyl salicylate | 75 g, |
| terpineol | 48 g, |
| dimethyl 3-cyclohexene-1-carboxaldehyde | 4 g, |
| vanillin | 2 g, |
| acetyl cedrene | 12 g, |
| sandalore | 12 g, |
| dimethyl benzyl carbinol butyrate | 1 g, |
| methyl 2,4-dihydroxy-3,6-dimethyl-benzoate | 13 g, |
| 9-decen-2-one | 10 g. |

In the presence of 9-decen-2-one, the cream has more head, with much more intense green and fresh notes.

Example 9

Toxicity Tests

The molecule was tested on 3 rabbits according to the experimental protocol established by "the OECD guideline No. 404 dated Apr. 24, 2002" and the test "method B.4 of the Directive No. 2004/73/EC): Acute dermal irritation".

It emerges therefrom that 9-decen-2-one is not irritant and that no hazard symbol or phrases are required for its use (according to the "EEC Directives 67/548/59 and 99/45").

Similarly, the molecule was tested on 3 rabbits according to the experimental protocol established by "the OECD guideline No. 405 dated Apr. 24, 2002" and the test "method B.5 of the Directive No. 2004/73/EC): Acute eye irritation".

It also emerges therefrom that 9-decen-2-one is not irritant and that no hazard symbol or phrases are required for its use (according to the "EEC Directives 67/548/59 and 99/45").

Finally, the value obtained in the LD50 test (acute oral toxicity (cf.: the same Directive), i.e. 2500 mg/kg), made it possible to classify the molecule as nonhazardous.

Due to its harmlessness, it thus appears that this molecule may be used in formulation and, due to its attested presence in mango and pineapple, it may be used in food flavoring and perfumery applications that may claim a "natural" label.

Although the present invention has been described above by means of examples of its preferred embodiments, it is understood that it can be modified without departing from the spirit and nature of the invention as defined in the attached claims.

The invention claimed is:

1. A process for producing 9-decen-2-one, characterized by the bioconversion of undecylenic acid using a mold, said process comprising the following steps:
   a) culturing said mold;
   b) adding the substrate undecylenic acid in the presence of a natural oil;
   c) bioconverting the substrate into 9-decen-2-one,
   d) extracting and purifying the 9-decen-2-one.

2. The process as claimed in claim 1, characterized in that said mold belongs to the family of Aspergillaceae.

3. The process as claimed in claim 2, characterized in that said mold belongs to the genus *Aspergillus* or to the genus *Penicillium*.

4. The process as claimed in claim 1, characterized in that said mold belongs to the family of Mortierellaceae or to the family of Mucoraceae.

5. The process as claimed in claim 4, characterized in that said mold belongs to the genus *Mortierella*, to the genus *Mucor* or to the genus *Rhizopus*.

6. The process as claimed in claim 1, characterized in that said undecylenic acid is added to the fermentation medium at a feed rate of 0.1 to 0.9 g/l/h.

7. The process as claimed in claim 1, characterized in that the bioconversion step comprises a first phase of adaptation of the mold in which said undecylenic acid is added at a feed rate of 0.1 to 0.5 g/l/h, and then a second phase in which the undecylenic acid is added at a feed rate of 0.25 to 0.9 g/l/h.

8. The process as claimed in claim 7, characterized in that the duration of said adaptation phase is less than 20 hours.

9. The process as claimed in claim 1, characterized in that said oil is chosen from the group comprising standard food-grade oils or triglycerides formed from short-chain fatty acids, or alternatively white oils.

10. The process as claimed in claim 1, characterized in that said oil is added to the fermentation medium at a feed rate of between 0.4 and 4.0 g/l/h.

11. The process as claimed in claim 1, characterized in that glucose or maltose is added simultaneously with the undecylenic acid and the oil.

12. The process as claimed in claim 11, characterized in that said glucose or said maltose is added to the fermentation medium at a feed rate of less than 1 g/l/h.

13. The process as claimed in claim 1, characterized in that the addition of said undecylenic acid, of said oil and optionally of said glucose or maltose to the fermentation medium is performed continuously for 5 to 96 hours.

14. The process as claimed in claim 1, characterized in that the bioconversion is performed at a temperature of between 25° C. and 35° C.

15. The process as claimed in claim 1, characterized in that the pH of the fermentation medium is between 5 and 8.

16. The process as claimed in claim 1, characterized in that the aeration of the fermentation medium is less than or equal to 1 vvm.

17. The process as claimed in claim 1, characterized in that the bioconversion is stopped by adding to the culture medium an acid chosen from the group comprising phosphoric acid, hydrochloric acid, sulfuric acid and citric acid.

18. The process as claimed in claim 8, wherein the duration of said adaptation phase is less than 12 hours.

19. The process as claimed in claim 8, wherein the duration of said adaptation phase is less than 6 hours.

20. The process as claimed in claim 12, wherein said glucose or said maltose is added to the fermentation medium at a feed rate of less than 0.75 g/l/h.

21. The process as claimed in claim 12, wherein said glucose or said maltose is added to the fermentation medium at a feed rate of less than 0.5 g/l/h.

22. The process as claimed in claim 14, wherein the bioconversion is performed at a temperature of between 27° C. and 30° C.

* * * * *